United States Patent [19]
Blomquist

[11] Patent Number: 5,485,408
[45] Date of Patent: Jan. 16, 1996

[54] PUMP SIMULATION APPARATUS

[75] Inventor: Michael L. Blomquist, Coon Rapids, Minn.

[73] Assignee: SIMS Deltec, Inc., St. Paul, Minn.

[21] Appl. No.: 276,025

[22] Filed: Jul. 15, 1994

Related U.S. Application Data

[63] Continuation of Ser. No. 942,288, Sep. 9, 1992, Pat. No. 5,338,157.

[51] Int. Cl.$^6$ .................................................. G06F 17/00
[52] U.S. Cl. ........................................ 364/578; 364/579
[58] Field of Search .................................... 364/578, 579, 364/580, 188, 413.02, 413.04; 395/157, 159

[56] References Cited

U.S. PATENT DOCUMENTS

| | | | |
|---|---|---|---|
| D. 294,733 | 3/1988 | Peterson et al. . | |
| 4,091,550 | 5/1978 | Shrenk et al. . | |
| 4,098,267 | 7/1978 | Stein et al. . | |
| 4,559,038 | 12/1985 | Berg et al. . | |
| 4,565,542 | 1/1986 | Berg . | |
| 4,606,353 | 8/1986 | Timm . | |
| 4,624,661 | 11/1986 | Arimond . | |
| 4,649,499 | 3/1987 | Sutton et al. . | |
| 4,650,469 | 3/1987 | Berg et al. . | |
| 4,656,603 | 4/1987 | Dunn | 364/159 |
| 4,731,058 | 3/1988 | Doan . | |
| 4,754,401 | 6/1988 | Kaczynski et al. . | |
| 4,756,706 | 7/1988 | Korns et al. | 364/413.02 |
| 4,778,449 | 10/1988 | Weber et al. . | |
| 4,832,033 | 5/1989 | Maher et al. . | |
| 4,847,764 | 7/1989 | Halvorson | 364/479 |
| 4,889,132 | 12/1989 | Hutcheson et al. . | |
| 4,898,578 | 2/1990 | Ruhalcaba | 364/188 |
| 4,933,873 | 6/1990 | Kaufman et al. . | |
| 4,954,818 | 9/1990 | Nakano et al. | 395/158 |
| 4,970,664 | 11/1990 | Kaiser | 395/157 |
| 5,032,978 | 7/1991 | Blomquist | 364/188 |
| 5,038,800 | 8/1991 | Oba . | |
| 5,078,683 | 1/1992 | Sancoff et al. . | |
| 5,084,828 | 1/1992 | Kaufman et al. . | |
| 5,100,380 | 3/1992 | Epstein et al. . | |
| 5,131,816 | 7/1992 | Brown et al. . | |
| 5,153,827 | 10/1992 | Coutre et al. . | |
| 5,172,698 | 12/1992 | Stanko . | |
| 5,224,051 | 6/1993 | Johnson . | |
| 5,247,434 | 9/1993 | Peterson et al. | 364/188 |
| 5,295,062 | 3/1994 | Fukushima | 364/188 |
| 5,301,301 | 4/1994 | Kodusky et al. | 364/578 |
| 5,363,482 | 11/1994 | Victor et al. | 395/159 |

FOREIGN PATENT DOCUMENTS

| | | |
|---|---|---|
| 0233115 | 9/1987 | European Pat. Off. . |
| 0319272 | 6/1989 | European Pat. Off. . |
| 2675288 | 10/1992 | France . |

*Primary Examiner*—Ellis B. Ramirez
*Attorney, Agent, or Firm*—Merchant, Gould, Smith, Edell, Welter & Schmidt

[57] ABSTRACT

The present invention relates to systems and methods for communicating with ambulatory medical devices, such as drug delivery devices, both locally and remotely. In one embodiment, a caregiver drug pump communicates with a remote patient drug pump for data gathering, trouble shooting, and operational program changes. The caregiver drug pump is at least substantially identical in configuration to the patient drug pump. The caregiver drug pump transmits caregiver key input signals to the remote patient drug pump. The patient drug pump receives the key input signals, accesses a desired program, and transmits information for display on the display of the caregiver drug pump. In another embodiment, a computer is provided for communicating locally and/or remotely with a drug pump. The computer may include a display with an image of a pump. The computer may be operated through the use of a mouse or touch screen with respect to the image of the pump, to simulate use of the pump while using the personal computer. The computer may also be used as a training aid for training a caregiver and/or patient how to use the drug pump.

10 Claims, 10 Drawing Sheets

| CAREGIVER PUMP | PATIENT PUMP |
|---|---|
| CAREGIVER CONNECTS CAREGIVER MODEM CABLE TO CAREGIVER PUMP AND INSTRUCTS PATIENT TO CONNECT PATIENT MODEM CABLE TO PATIENT PUMP. | |
| PUMP TELLS MODEM TO TURN ON SPEAKER | PATIENT CONNECTS PATIENT MODEM CABLE TO PATIENT PUMP |
| CAREGIVER ASKS PATIENT TO VERIFY THAT PATIENT PUMP HAS RESPONDED WITH "PRESS ENTER TO START SLAVE COMMUNICATIONS" MESSAGE ON THE DISPLAY. CAREGIVER INSTRUCTS PATIENT TO PRESS ENTER KEY, THEN, WITHOUT HANGING UP THE PHONE, TO LISTEN FOR FURTHER INSTRUCTIONS, COMING FROM THE MODEM SPEAKER. | |
| | PATIENT PRESSES ENTER KEY |
| | PUMP TELLS MODEM TO START SLAVE COMMUNICATIONS. PUMP STARTS TWO MINUTE TIME OUT WHILE WAITING FOR CARRIER DETECT FROM MODEM. |
| | MODEM GOES OFF-HOOK |
| | MODEM DISCONNECTS PHONE |
| | MODEM TURNS ON SPEAKER |
| | MODEM SENDS SHORT BEEP TO CAREGIVER PUMP THEN LISTENS FOR CARRIER |

FIG. 6A

| 302 | 304 |
|---|---|
| CAREGIVER HEARS SHORT MODEM BEEP EITHER FROM PHONE HANDPIECE OR MODEM SPEAKER AND KNOWS THAT THE PATIENT PUMP IS READY | PATIENT SETS PHONE DOWN WITHOUT HANGING UP |
| CAREGIVER PRESSES ENTER KEY | |
| PUMP TELLS MODEM TO START MASTER COMMUNICATIONS, THEN PUMP WAITS FOR INCOMING DATA. PUMP STARTS TWO MINUTE TIME OUT WHILE WAITING FOR RESPONSE FROM PATIENT PUMP | |
| MODEM GOES OFF-HOOK | |
| MODEM DISCONNECTS PHONE | |
| MODEM SENDS CARRIER | |
| CAREGIVER SETS PHONE DOWN WITHOUT HANGING UP | MODEM RECEIVES CARRIER, THEN SENDS "CARRIER RECEIVED" SIGNAL TO PATIENT PUMP |
| | PUMP TELLS MODEM TO SHUT OFF SPEAKER |
| | MODEM SHUTS OFF SPEAKER |
| | PUMP SENDS "I'M HERE" SIGNAL TO CAREGIVER PUMP |
| PUMP ACKNOWLEDGES "I'M HERE" SIGNAL AND SENDS "OK TO BEGIN" SIGNAL TO PATIENT PUMP | |
| PUMP TELLS MODEM TO SHUT OFF SPEAKER | PATIENT PUMP RECEIVES "OKAY TO BEGIN" SIGNAL AND SENDS CURRENT DISPLAY SIGNAL TO CAREGIVER PUMP |
| MODEM SHUTS OFF SPEAKER | |
| PUMP SENDS KEY INPUT SIGNALS TO PATIENT PUMP | PUMP SENDS DISPLAY SIGNALS TO CAREGIVER PUMP IN RESPONSE TO KEY INPUT SIGNALS |

FIG. 6B

| CAREGIVER PUMP | PATIENT PUMP |
|---|---|
| CAREGIVER PRESSES STOP/START KEY | |
| PUMP SENDS "DISCONNECT" SIGNAL TO PATIENT PUMP | |
| PUMP SENDS "DISCONNECT" SIGNAL TO MODEM | PUMP ACKNOWLEDGES "DISCONNECT" SIGNAL |
| MODEM CUTS CARRIER | PUMP BEGINS TO BEEP |
| MODEM CONNECTS PHONE | PUMP SENDS "DISCONNECT" SIGNAL TO MODEM |
| MODEM TURNS ON SPEAKER | MODEM CUTS CARRIER |
| | MODEM CONNECTS PHONE |
| | MODEM TURNS ON SPEAKER |
| CAREGIVER UNPLUGS CAREGIVER MODEM CABLE | |
| MODEM DISCONNECTS SPEAKER | |
| MODEM GOES ON HOOK | |
| CAREGIVER PICKS UP PHONE THEN CALLS FOR PATIENT TO PICK UP PHONE. | |
| | PATIENT HEARS CAREGIVER IN MODEM SPEAKER AND PICKS UP PHONE |
| CAREGIVER TELLS PATIENT TO DISCONNECT PATIENT MODEM CABLE | |
| | PATIENT DISCONNECTS PATIENT MODEM CABLE |
| | PUMP STOPS BEEPING |
| | MODEM DISCONNECTS SPEAKER |
| | MODEM GOES ON HOOK |
| CAREGIVER RESUMES NORMAL VOICE COMMUNICATIONS | PATIENT RESUMES NORMAL VOICE COMMUNICATIONS |

FIG. 7

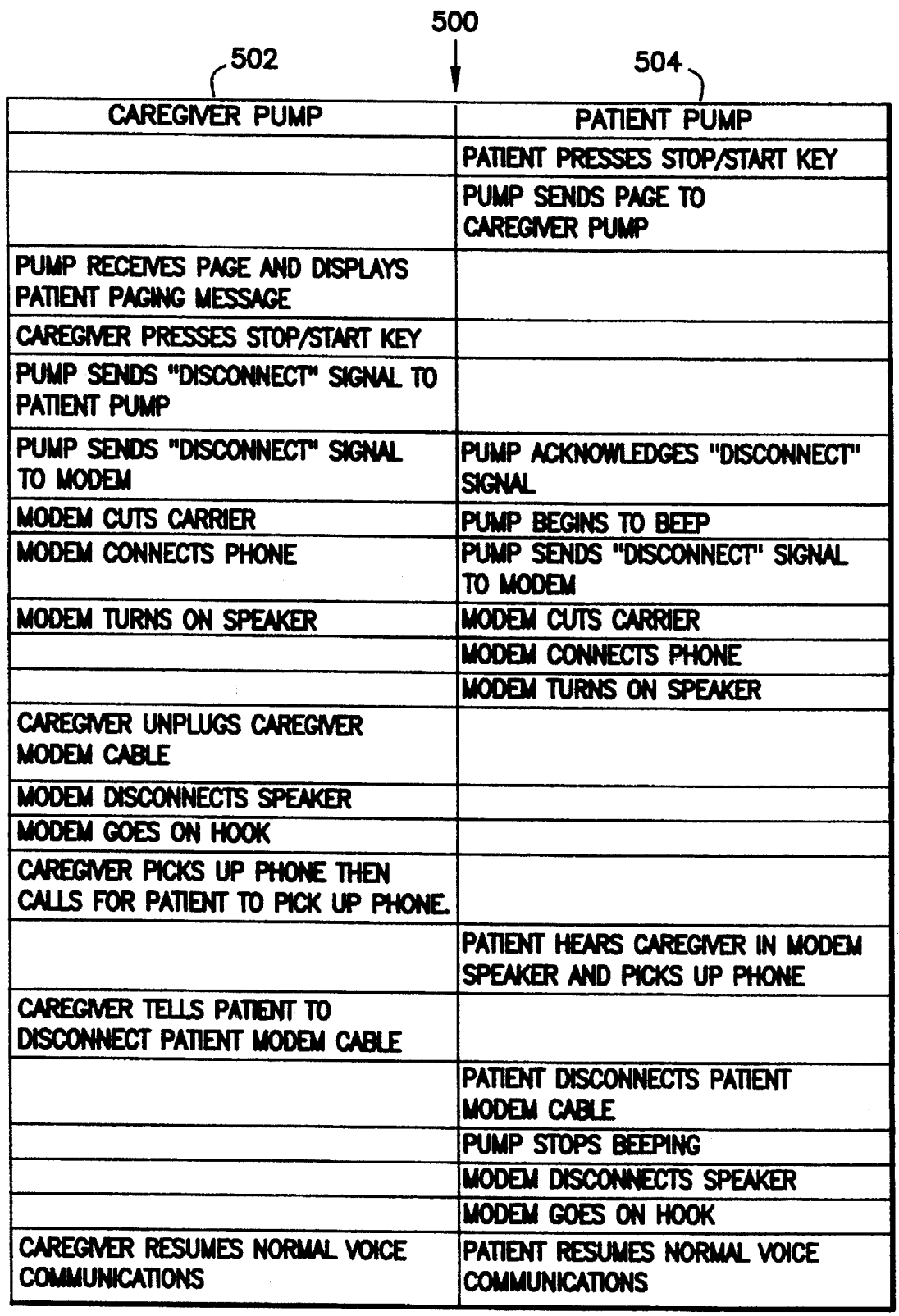

| CAREGIVER PUMP | PATIENT PUMP |
|---|---|
| | PATIENT PRESSES STOP/START KEY |
| | PUMP SENDS PAGE TO CAREGIVER PUMP |
| PUMP RECEIVES PAGE AND DISPLAYS PATIENT PAGING MESSAGE | |
| CAREGIVER PRESSES STOP/START KEY | |
| PUMP SENDS "DISCONNECT" SIGNAL TO PATIENT PUMP | |
| PUMP SENDS "DISCONNECT" SIGNAL TO MODEM | PUMP ACKNOWLEDGES "DISCONNECT" SIGNAL |
| MODEM CUTS CARRIER | PUMP BEGINS TO BEEP |
| MODEM CONNECTS PHONE | PUMP SENDS "DISCONNECT" SIGNAL TO MODEM |
| MODEM TURNS ON SPEAKER | MODEM CUTS CARRIER |
| | MODEM CONNECTS PHONE |
| | MODEM TURNS ON SPEAKER |
| CAREGIVER UNPLUGS CAREGIVER MODEM CABLE | |
| MODEM DISCONNECTS SPEAKER | |
| MODEM GOES ON HOOK | |
| CAREGIVER PICKS UP PHONE THEN CALLS FOR PATIENT TO PICK UP PHONE. | |
| | PATIENT HEARS CAREGIVER IN MODEM SPEAKER AND PICKS UP PHONE |
| CAREGIVER TELLS PATIENT TO DISCONNECT PATIENT MODEM CABLE | |
| | PATIENT DISCONNECTS PATIENT MODEM CABLE |
| | PUMP STOPS BEEPING |
| | MODEM DISCONNECTS SPEAKER |
| | MODEM GOES ON HOOK |
| CAREGIVER RESUMES NORMAL VOICE COMMUNICATIONS | PATIENT RESUMES NORMAL VOICE COMMUNICATIONS |

FIG. 8

PUMP SIMULATION APPARATUS

This is a continuation of application Ser. No. 07/942,288, filed Sep. 9, 1992, U.S. Pat. No. 5,338,157, which application are incorporated herein by reference.

FIELD OF THE INVENTION

The present invention relates generally to ambulatory medical devices and methods for communicating with such devices. In particular, the present invention relates to systems and methods for locally and remotely communicating with drug delivery devices.

BACKGROUND OF THE INVENTION

Various ambulatory medical devices are known for treating and/or monitoring patients at a remote site away from the caregiver's or clinician's office. One example of an ambulatory medical device is a drug delivery device, such as a drug pump, for providing periodic or continuous drug delivery to the patient when the patient is away from the caregiver's office.

Certain drugs rarely achieve their maximum therapeutic action through conventional injection techniques. Many drugs reach their full potential only through precise delivery over an extended period of time. With controlled drug infusion through a drug pump, the drug can be given at a precise rate that will keep the drug concentration within the therapeutic margin and out of the toxic range. Ambulatory drug pumps can provide appropriate drug delivery to the patient at a controllable rate which does not require frequent medical attention and which allows the patient to leave the hospital or caregiver's office.

A failure to adequately monitor the drug pump and the patient's usage of the drug pump can reduce or eliminate any benefits the patient may have received from a proper drug delivery therapy. In some cases, the drug therapies can have serious health consequences to the patient if the drugs are not administered properly.

Several concerns arise when the patient utilizes the various ambulatory medical devices at remote sites. If the ambulatory medical device gathers data with respect to the device and/or the patient, the data needs to be easily accessible by the caregiver to permit the caregiver to monitor the device and the patient. Often, the patient may be of little or no assistance in accessing the data and communicating with the caregiver from the remote site. If the caregiver needs to physically handle the device to access the data, the device and caregiver must be brought to the same location.

Similar problems can also arise in that the medical devices may fail or be used improperly at the remote sites. If the device is not operating properly, the device may have to be brought to the caregiver, or the caregiver may have to visit the patient. If the caregiver attempts to trouble shoot from a remote site, the patient may be unable physically or mentally to sufficiently cooperate with the caregiver for the caregiver to trouble shoot from the remote site. Operating problems can arise at inconvenient times, such as at night or on weekends and holidays. The caregiver may also need to be able to easily periodically monitor the patient's usage of the medical device to observe patient compliance with prescribed treatments while the patient is at the remote site.

There may further arise a need for the caregiver to access the controller, such as the processor and the programs, which controls operation of the ambulatory medical devices. For example, in the case of drug delivery devices, some therapies change over time. The caregiver may need to access the operating program in order to change the operation of the drug delivery device. Further, some drug delivery devices, for example, may be used for very different applications, requiring different operating programs. These operating programs can be changed as the use of the drug delivery device changes. Resources may not be used efficiently if the caregiver and the device must be brought to the same location for the caregiver to access the processor and operating programs.

One specific situation often arises in the case of a drug pump where the caregiver needs to access the controller of the drug pump. The caregiver may visit the patient at the patient's home at some point after the drug therapy has begun using the drug pump. The caregiver may sample the patient's blood. The caregiver returns to the office and the blood sample is analyzed. The results of the blood analysis may indicate the patient is not receiving the proper drug therapy. This usually means the controller of the drug pump must be adjusted to give the proper therapy to the specific patient. To adjust the controller, the caregiver needs to be able access the controller.

Another problem facing caregivers in the area of ambulatory medical devices relates to the ease of remote communication with the devices, if such remote communication capability is provided. Remote communication with an ambulatory medical device using a personal computer or base station may be difficult for some caregivers, if the personal computer/base station operates differently than the medical device. The caregiver must then be knowledgeable both in operation of the medical device and in operation of the personal computer/base station. This concern also applies to local communication with the ambulatory medical device.

In the case of remote communication with a patient's medical device using a personal computer/base station, the caregiver also needs to remain near the personal computer/base station, or else transport the personal computer/base station with the caregiver, if the caregiver wishes to remain in communication with the patient's medical device.

It sometimes may become necessary to communicate with a personal computer or base station either locally or remotely in order to take advantage of the greater data handling or processing capability of the personal computer or base station, for example. The ability of the caregiver to communicate easily with the pump using a personal computer or base station may be important in those circumstances. In addition, the patient may be able to do very little to assist the caregiver in linking the remote medical device to the local personal computer/base station.

There is a need for systems and methods for communicating with ambulatory medical devices such as drug delivery devices, both locally and remotely, which addresses the above concerns and other concerns.

SUMMARY OF THE INVENTION

The present invention relates to systems and methods for communicating with an ambulatory medical device, such as a drug delivery device, and in particular, a drug pump. In one embodiment, a communication system is provided where a remote drug pump communicates with a similar local drug pump. Each of the drug pumps are provided with a pump controller for controlling operation of the pump. The controller may include a processor and associated memory for storing operating programs and other information. The pumps each include a pumping mechanism controlled by the controller for pumping fluid to a patient in the normal pumping mode of operation.

Interconnect structure, such as modems, is provided to permit interconnection of the controllers of the pumps in the pump to pump communications mode of operation. The interconnect structure permits communication between the respective processors over a communications medium, such as conventional telephone communication lines. The telephone lines also permit initial voice communication between the patient and the caregiver using conventional telephones or other devices before the pumps are linked together for the pump to pump communications mode of operation. The modems may include speakers to facilitate ease of operation during pump to pump communication with patients who have difficulty in cooperating with the caregiver due to mental and/or physical limitations.

Each drug pump includes operator input structure for making operator inputs to the controller of the respective pump. The operator input structure is useful for selecting desired pump control programs or desired pump data or both from the memory of the processor of the pump. The information selection structure may include a keypad comprising a plurality of keys.

Display structure on each pump is interconnected to the controller of the respective pump. The display structure displays information about operations of the pump sent to the display structure by the controller. The display structure may display desired information from the memory of the processor, such as information relating to the normal pumping operations mode of the pumping mechanism. Other information that may be displayed may relate to various sensor outputs to the controller. Other information displayed may relate to the pump to pump communications mode. The display structure may include an LCD dot matrix display.

Information programmed into the controllers allows the two pumps to communicate in such a way during pump to pump communications that one pump controls the functions of the other. Information programmed into the local drug pump, or caregiver pump, instructs that the caregiver pump be put into the master mode at some point during operation. In the master mode, the local caregiver pump sends its keyboard inputs to a remote patient pump. The caregiver pump also receives its display inputs from the remote patient pump. The caregiver pump is used by the caregiver for such purposes as data gathering, trouble shooting, and operational program changes with respect to the remote patient pump. Ease of communication is provided since the caregiver is likely already familiar with operation of the patient pump, thereby saving training time because the caregiver pump operates similarly to the patient pump. Further, the caregiver can remain in constant communication with the patient pump by merely transporting the caregiver pump and a modem with the caregiver at all times.

The remote patient pump has information programmed into the controller that instructs the patient pump to be put into the slave mode at the appropriate time. In the slave mode, the patient pump receives its keyboard input signals primarily from the caregiver pump. The patient pump sends its display signals to the caregiver pump. In one embodiment, the slave mode of the patient pump disables the patient pump from actually pumping the fluid during communication with the caregiver pump.

In one embodiment, the caregiver pump and the patient pump both include program means for operating in both the master and slave modes. Automatic selection of the master or slave mode from the normal pumping mode is provided when a communications cable is connected to the respective pump.

Various program means and sequences are disclosed for communication between the local caregiver pump and the remote caregiver pump to facilitate efficient communication while emphasizing easy usage by the caregiver and by the patient, some of whom may have difficulty carrying out instructions from the caregiver over the telephone.

In another embodiment, systems and methods are provided for communicating between a remote pump and a local caregiver computer, such as a personal computer. Such communication may permit greater data processing utilizing the computer's data handling capability. Also, communication with the remote pump using the local computer may be useful for recertifying the remote pump periodically as is sometimes required with respect to medical devices. The local computer may also be useful in changing or adjusting the pump operations program of the remote pump. Modem communication structure permits communication over a communications medium, such as conventional telephone lines, between the remote pump and the local computer.

In a further embodiment, modem communication structure is provided which links a local pump to a local computer. Preferably, the modem communication structure also includes structure for further permitting communication between the local computer or the local pump and a remote pump. This modem communication structure permits: (1) local pump and local computer communication; (2) local pump and remote pump communication; and (3) remote pump and local computer communication.

In another embodiment of the invention, a computer system is provided, with a processor and memory, which is programmed to display an image of a pump on a display that resembles the pump utilized by the patient. The image includes representations of the keys and the display of an actual pump. The computer is further programmed such that the image of the pump is utilized to communicate with an actual remote pump or an actual local pump by manipulating or activating the keys on the image of the pump. The keys of the image can be activated by such techniques as through the use of a mouse or a touch screen. Activating the keys of the image of the pump simulates for the caregiver the presence of an actual pump. This facilitates reductions in training time for training the caregiver to communicate with the patient's pump, since the caregiver is most likely already familiar with operation of the patient's pump.

The computer system with the pump image program may also be used as a simulator for training the caregiver or the patient how to use the pump. The simulator includes various programs for simulating for the patient trainee and/or the caregiver trainee various pump operations situations with a patient's pump for pumping fluid. The simulator also includes various programs for simulating for the patient trainee and/or the caregiver trainee various communication situations with a patient's pump.

These and other features of the present invention are described in greater detail in the detailed description of the preferred embodiments.

BRIEF DESCRIPTION OF THE DRAWINGS

In the drawings, where like numerals refer to like features throughout the several views:

FIGS. 6A and B comprise a single flow chart of operational sequences involving the caregiver pump and the patient pump during connection and communication between the caregiver pump and the patient pump when the patient pump is located at a remote site. FIG. 6B follows after FIG. 6A during operations.

FIG. 7 is a flow chart of operational sequences involving the caregiver pump and the patient pump when the caregiver wants to discontinue communication between the caregiver pump and the patient pump at some time during remote communication between the caregiver pump and the patient pump.

FIG. 8 is a flow chart of operational sequences involving the caregiver pump and the patient pump when the patient wishes to speak to the caregiver at some time during remote communication between the caregiver pump and the patient pump.

DESCRIPTION OF THE PREFERRED EMBODIMENTS

Figure 1:
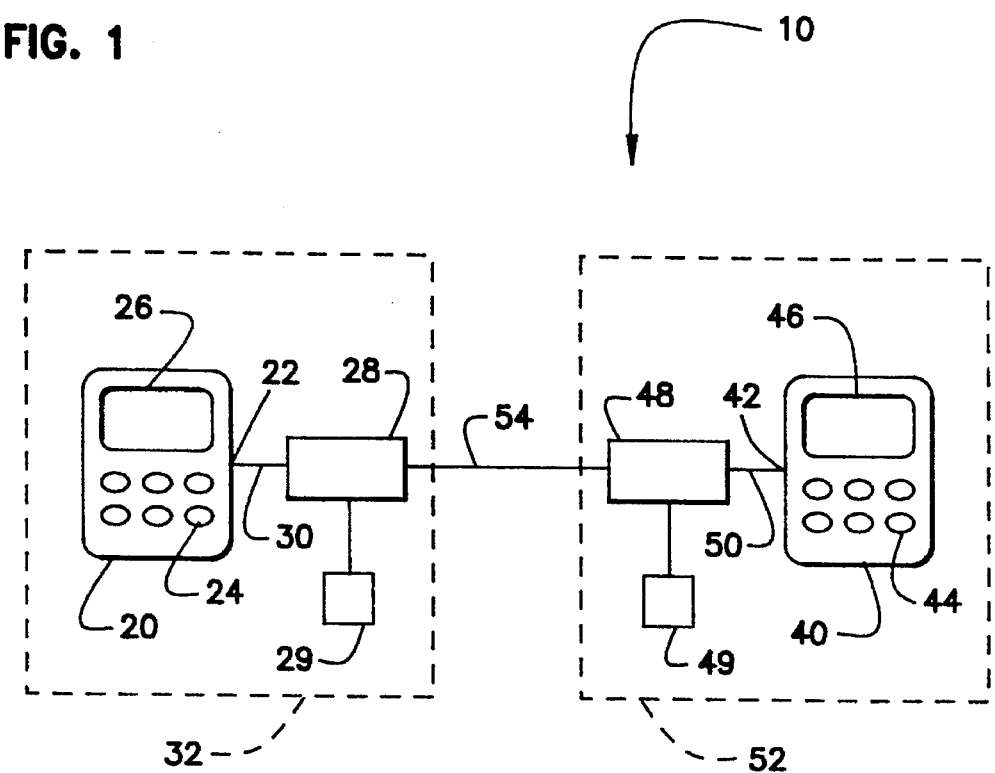
FIG. 1 is a schematic diagram illustrating a first system of local pump and remote pump communications.

Referring now to FIG. 1, a system 10 of communication between a local drug pump 20 (or caregiver pump) and a remote drug pump 40 (or patient pump) is shown. In system 10, local pump 20 is functioning as a caregiver pump for use by the caregiver at the site 32 where the caregiver is located, such as the caregiver's office. Site 32 may be the caregiver's home, during on call periods, or even the caregiver's automobile, if the automobile is provided with some communications capability for sending and receiving signals with respect to another site. In system 10, the caregiver operating pump 20 is typically a nurse, physician, therapist, or other medical personnel.

In system 10, remote pump 40 is functioning as an ambulatory patient pump for pumping drugs to the patient and is located with the patient at a site remote from caregiver pump 20, such as at the patient's home 52. Also, site 52 may be the patient's workplace.

Pumps 20,40 each include a pumping mechanism which is capable of pumping fluid from a fluid reservoir to a patient. Specific components of patient pump 40 are shown in greater detail in FIG. 1A. Caregiver pump 20 is preferably identical to patient pump 40 with respect to the features shown in FIG. 1A.

Figure 1A:
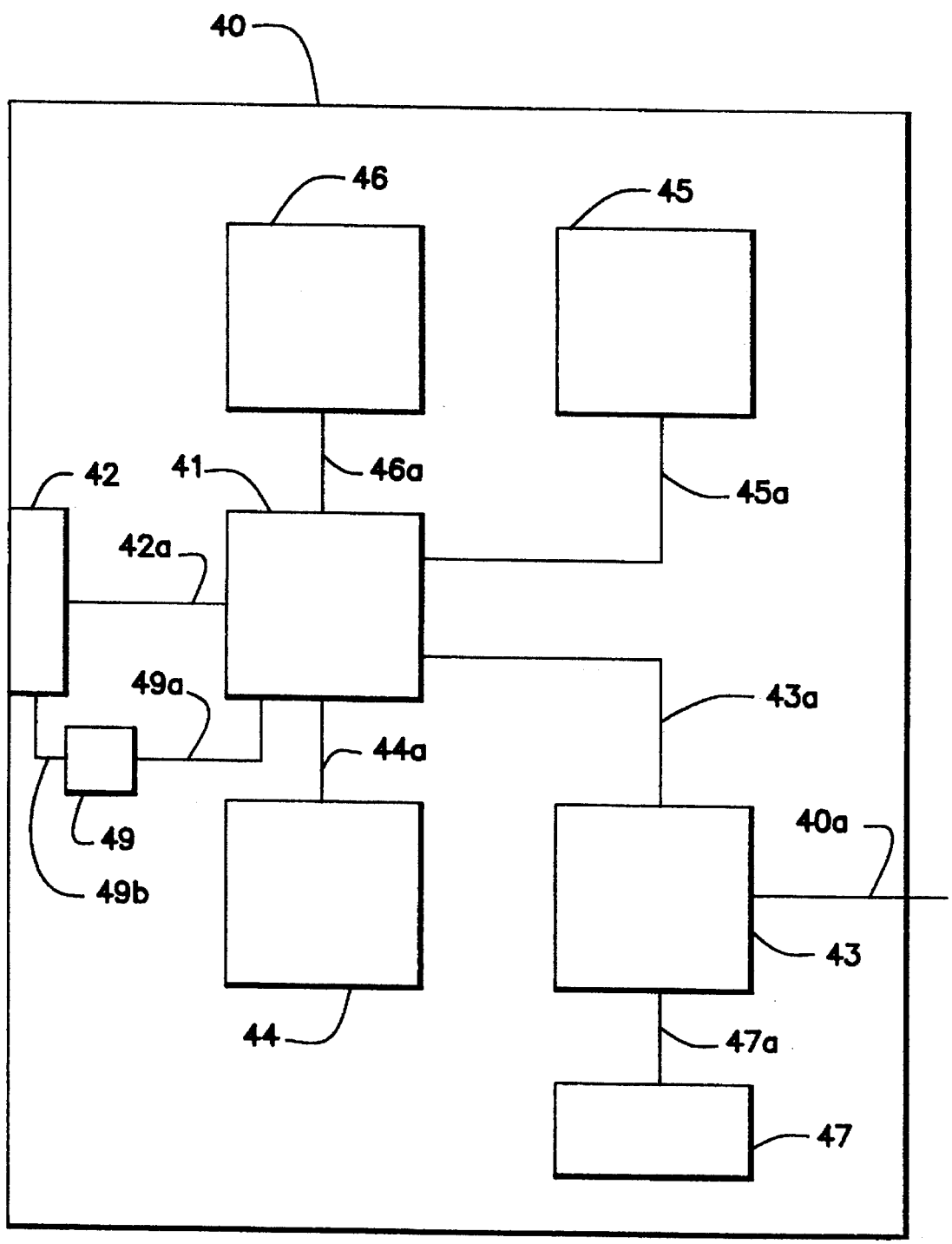
FIG. 1A is a schematic diagram illustrating components of the remote pump shown in FIG. 1.

Pump 40 as shown in FIG. 1A includes a pumping mechanism 43 and a fluid reservoir 47 interconnected by a fluid communication structure 47a, such as a tube. The fluid reservoir 47 may be a cassette mounted to pump 40, or the fluid reservoir may be a container located at a remote site from pump 40, both interconnected to pump 40 with a fluid communication tube 47a. To pump fluid to a patient, the pump is also interconnected to the patient, such as through a tube 40a. The pumping mechanism 43 pumps fluid from the reservoir 47 to the patient through the tube 40a interconnected to the patient.

Pumps 20,40 may be any of a variety of drug delivery pumps. An example of one drug delivery pump is described in U.S. Pat. No. 4,559,038, incorporated herein by reference. In U.S. Pat. No. 4,559,038, a rotating camshaft is provided which engages two reciprocating valves and a reciprocating expulser. The valves and expulser engage a tube interconnected in fluid communication between a fluid reservoir and the patient. The rotating camshaft moves the valves and expulser to pump fluid through the tube.

In the communication system 10 of FIG. 1, only patient pump 40 is utilized to pump fluid to the patient. Caregiver pump 20 is used by the caregiver to communicate with patient pump 40. Caregiver pump 20 is preferably not used to pump fluid during pump to pump communication with patient pump 40. However, caregiver pump 20 could be used to pump fluid to a patient before or after communication with patient pump 40, should the need arise. In some cases, caregiver pump 20 could be used to pump fluid during pump to pump communications with patient pump 40.

Pumps 20,40 each include a controller for controlling operation of the pumping mechanism utilized to pump fluid. Pump 40 shown in greater detail in FIG. 1A includes a controller 41 interconnected to pumping mechanism 43 through connection structure 43a. The controller 41 preferably includes a processor and memory programmable with selected functions for controlling operation of the pumping mechanism 43. As shown in FIG. 1A, the controller 41 is also connectable to one or more electrical sensor elements in the pump, such as sensors 45,49.

A variety of sensors like sensor 45 may be provided depending on the type of pump and the intended usage of the pump. For example, since the fluid is pumped through a tube 40a to the patient by the pump, the pump may include a downstream high pressure sensor to detect when an occlusion of the tube has occurred. A sensor may also be provided to sense when a vacuum develops in tube 47a upstream from the pump between the pump mechanism 43 and the fluid reservoir 47, indicating a lack of fluid to be pumped. Other sensors may be provided to sense pump electrical power supply status. Still other sensors may be provided to monitor the operation of the mechanical components comprising the pumping mechanism. The sensors, like sensor 45, all typically send a suitable electrical signal to the processor of controller 41 through connection structure, like structure 45a, indicative of the conditions sensed. The controller is appropriately programmed to receive and process the sensor signals it receives. Sensor 49 relates a particular sensor useful during pump to pump communications to assist the operators (both patient and caregiver) in communication between the pumps, which will be discussed in greater detail below.

The controller 41 includes memory for storing various programs and data related to operation of the pump. The processor runs the desired operating programs to control operation of the pumping mechanism 43. The processor further responds to the sensor input signals by generating appropriate control output signals in accordance with its programmed control logic. Access to the processor is provided through an external communication port 42. For caregiver pump 20, access to the processor is provided through an external communication port 22 (see FIG. 1).

Both caregiver pump 20 and patient pump 40 can be utilized for pumping or delivering a drug to a patient when the respective pump is interconnected to the patient. Pumps 20,40 are preferably identical with respect to the electrical and the mechanical fluid pumping functions. One advantage of this is that caregiver pump 20 can be an unused spare patient pump 40. As will be discussed below, the respective controllers of pumps 20,40 may be programmed differently to operate in the appropriate desired manner during pump to pump communications. As will also be discussed, this programming can be done locally or remotely. Preferably, pumps 20,40 include appropriate programs to operate either as a master pump or as a slave pump during pump to pump communications. In some cases, the programs in each pump that control operation of the pumping mechanism will be different. This will also be discussed in more detail below.

One preferred processor that may be used in connection with pumps 20,40 is a MC68HC11E9 high-density complimentary metal-oxides semiconductor (HCMOS) high-performance microcontroller unit (MCU) by Motorola. Such processor includes 512 bytes of electrically erasable programmable ROM (EEPROM), and 512 bytes of RAM.

Pumps 20,40 each include operator input structure for permitting an operator of the respective pump to communicate with the controller of the pump, specifically the internal processor of the pump and the information in the internal memory. In one preferred embodiment, a plurality of operator keys 24 on caregiver pump 20 are provided for pressing by the caregiver. Preferably, each key has at least one function. Keys 24 send a signal to the controller of caregiver pump 20 indicative of the key pressed by the caregiver. The controller of pump 20 responds in the desired manner if an acceptable key press is made by the caregiver.

Patient pump 40 has keys 44 preferably identical to keys 24. Keys 44 send a signal to the controller of patient pump 40 indicative of the key pressed. The controller of patient pump 40 responds in the desired manner if an acceptable key press is made by the patient. As shown in FIG. 1A, keyboard 44 is interconnected to controller 41 through connection structure 44a.

Caregiver pump 20 includes a display 26 for displaying selected information stored in the controller. In one preferred embodiment, the display 26 includes an LCD dot matrix display. LCD dot matrix display 26 is interconnected to the controller of caregiver pump 20. Display signals sent from the controller of caregiver pump 20 permit display of information related to operation of pump 20 on display 26. One preferred LCD dot matrix display is a display with four lines and twenty-one characters per line.

Patient pump 40 has a display 46 preferably identical to display 26 of caregiver pump 20. Display signals sent from the controller of patient pump 40 display information related to operation of pump 40 on display 46. As shown in FIG. 1A, display 46 is interconnected to controller 41 through connection structure 46a.

Communication port 22 of caregiver pump 20 permits interconnection of the controller of caregiver pump 20 to a modem 28 located locally with respect to caregiver pump 20. Caregiver pump 20 is interconnected to modem 28 through connection structure 30, such as an RS232 serial cable. Caregiver pump 20 and modem 28 may be located at the caregiver's office 32, at the caregiver's home during on-call periods, or even at a mobile site, such as the caregiver's automobile.

Communication port 42 permits interconnection of the controller of patient pump 40 to modem 48 with connection structure 50, such as an RS232 serial cable. Patient pump 40 and modem 48 are both located remotely to caregiver pump 20 and modem 28, such as at the patient's home or workplace 52, or other location remote from caregiver pump 20.

Communication between pump 20 and pump 40 through modems 28,48 is over communications medium 54 such as conventional telephone lines, cellular phones, fiber optics links, satellite links, microwave links, or other. Modems 28,48 preferably communicate at 9600 bps and include error correction and data compression features over conventional telephone lines.

One advantage of the present invention is that the caregiver can communicate with the patient pump 40 using a similar pump, the caregiver's pump 20. The caregiver presumably has knowledge of operation of patient pump 40. This knowledge is useful in utilizing caregiver pump 20 to communicate with patient pump 40 to access the processor of patient pump 40 from a remote location.

Communication between the controller of the remote patient pump 40 and the controller of the local caregiver pump 20 permits remote data gathering from the remote patient pump by the local caregiver pump. Such data gathering may be useful for periodic monitoring of the patient pump 40 during use of the patient pump at the remote site. Data gathering may also be useful at the end of the patient use.

Communication between the remote patient pump 40 and the local caregiver pump 20 permits troubleshooting with respect to the remote patient pump, without the caregiver being located at the same location as the patient's pump. Remote troubleshooting is useful in the case where patients are unfamiliar with the some of the more sophisticated operations of their pump. Also, remote troubleshooting using the pump to pump communication system is useful for patients who have difficulty orally communicating with the caregiver over the telephone.

Communication with the remote patient pump 40 is also useful for accessing the pump operations programs for changing or adjusting the operation of the remote patient pump from the local site, thereby saving the caregiver and the patient time from not having to make an in-person visit.

Information programmed into the controller of the caregiver pump 20 permits the caregiver pump 20 to be put into a master mode from the normal pumping mode at the appropriate time. In the master mode, caregiver pump 20 sends a keyboard input signal indicative of a key 24 pressed by the caregiver over port 22 to patient pump 40. In the master mode, caregiver pump 20 receives its display signals primarily from patient pump 40 via communication port 22. In the master mode, the key presses on keys 24 of caregiver pump 20 do not access the memory of caregiver pump 20 for the purposes of programming the memory of caregiver pump 20 or selecting information for display relating to caregiver pump 20. The master mode is primarily for permitting caregiver pump 20 to communicate with the controller of patient pump 40 for the purposes of programming the memory of patient pump 40 or selecting information for display relating to patient pump 40 from the memory of patient pump 40.

With respect to patient pump 40, information programmed into its controller permits patient pump 40 be put into a slave mode from the normal pumping mode at the appropriate time. In the slave mode, patient pump 40 receives keyboard input signals primarily from caregiver pump 20 via communication port 42. Patient pump 40 sends its display signals from communication port 42 to caregiver pump 20.

To communicate between caregiver pump 20 and patient pump 40 over modems 28,48, caregiver pump 20 is out of the normal pumping mode and in the master mode. Similarly, patient pump 40 is out of the normal pumping mode and in the slave mode. In some cases, controllers with sufficient capacity may be provided where the pumps 20,40 operate simultaneously in the normal pumping mode and in the master or slave modes.

In system 10, patient pump 40 is at least programmed to be operable in two modes, the normal pumping mode and the slave mode. There typically is not a need for patient pump 40 to operate in the master mode when the patient possesses the patient pump. Further, in system 10, caregiver pump 20 is at least operable in the master mode. However, situations are anticipated where it is desireable to have one or both pumps 20,40 include programs for operation in the normal pumping mode, the slave mode, and the master mode. In some cases, caregiver pump 20 may be an unused patient spare. At a later date, the unused patient spare may be needed as a patient pump. This would require the slave mode operating program, and a particular normal operation mode program suitable for the patient. It may be more efficient for the caregiver if the controller of each pump 20,40 is preprogrammed to include both the master mode program and the slave mode program. The selection of master or slave mode may be made by the caregiver by preconfiguring the patient's pump 40 to enter the slave mode during pump to pump communication, and not enter the master mode. The caregiver would have the capability to preconfigure the caregiver pump 20 to only enter the master mode during pump to pump communication, and not the slave mode if the caregiver desired. At some point later in time, the caregiver could reconfigure the caregiver pump 20 to only enter the slave mode during pump to pump communications if the caregiver pump 20 was needed as a patient pump.

In system 10 of FIG. 1 which shows linking caregiver pump 20 to patient pump 40, the caregiver is able to access the controller of patient pump 40, make various inputs using the caregiver's pump 20, and receive back display inputs from patient pump 40 such that the caregiver can see the display inputs on the display 26 of caregiver pump 20. Such communication can occur when the patient pump 40 is located at a remote site from caregiver pump 20. This is particularly advantageous in saving resources by reducing the number of in-person visits between the caregiver and the patient.

In one embodiment, disabling structure is provided with respect to caregiver pump 20 for disabling the pumping mechanism of caregiver pump 20 such that during pump to pump communications, the pumping mechanism is disabled. Similarly, for patient pump 40, disabling structure is provided to disable the pumping mechanism of patient pump 40 during pump to pump communications. This may be necessary due to processor capability limitations. This may also be a safety feature to prevent a caregiver from starting operation of the patient's pump from the remote site. However, in some situations it may be desirable for caregiver pump 20 to begin operation of the pumping mechanism of patient pump 40 at a site remote from the location of the caregiver during pump to pump communications. If a suitable controller is provided, it may be possible to operate the pumping mechanism of patient pump 40 while patient pump 40 is communicating with caregiver pump 20.

Figure 4:
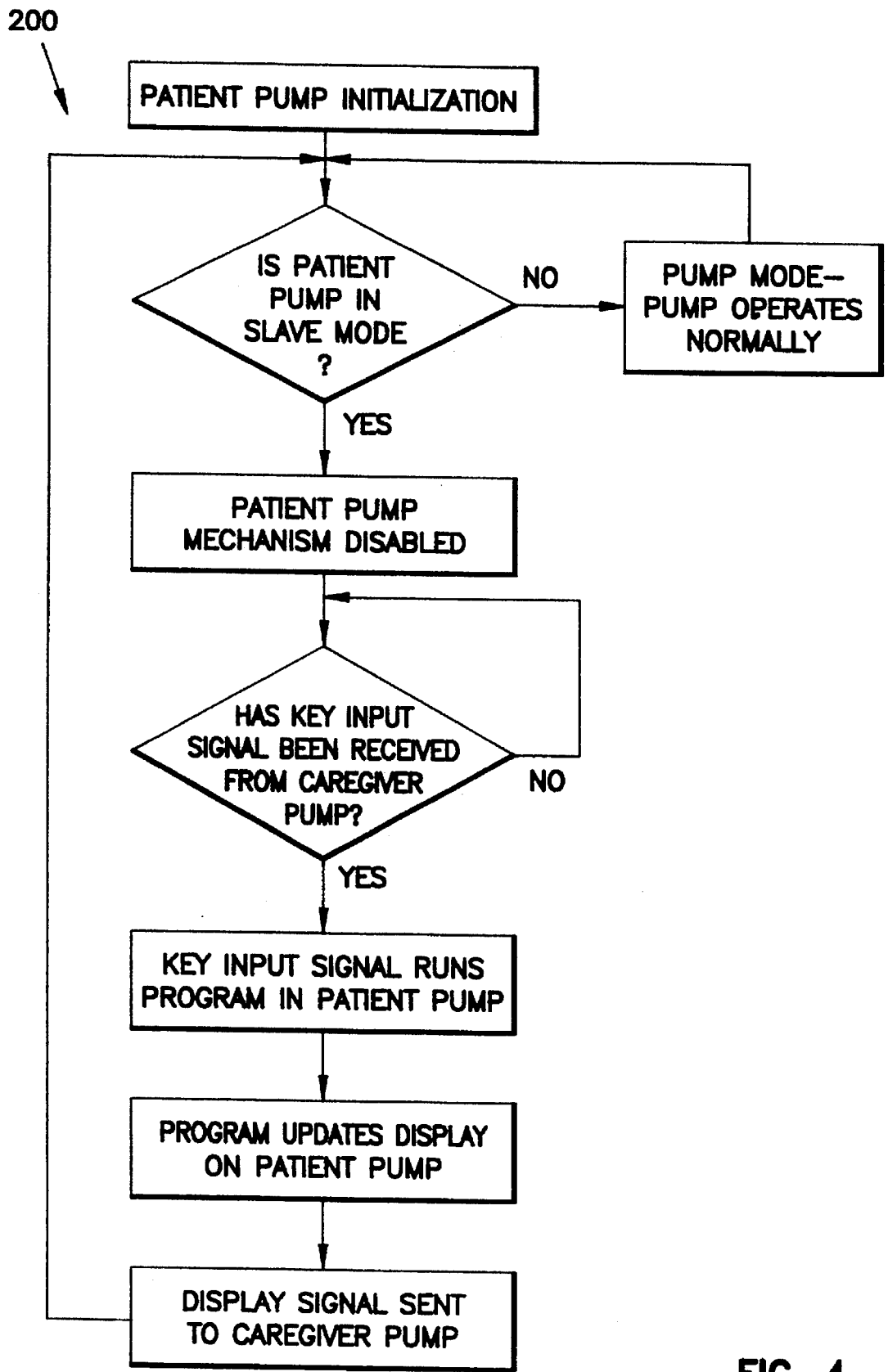
FIG. 4 is a flow chart of an operational sequence of the patient pump with respect to the normal pumping mode for pumping fluid and the slave mode for pump to pump communication.
Figure 5:
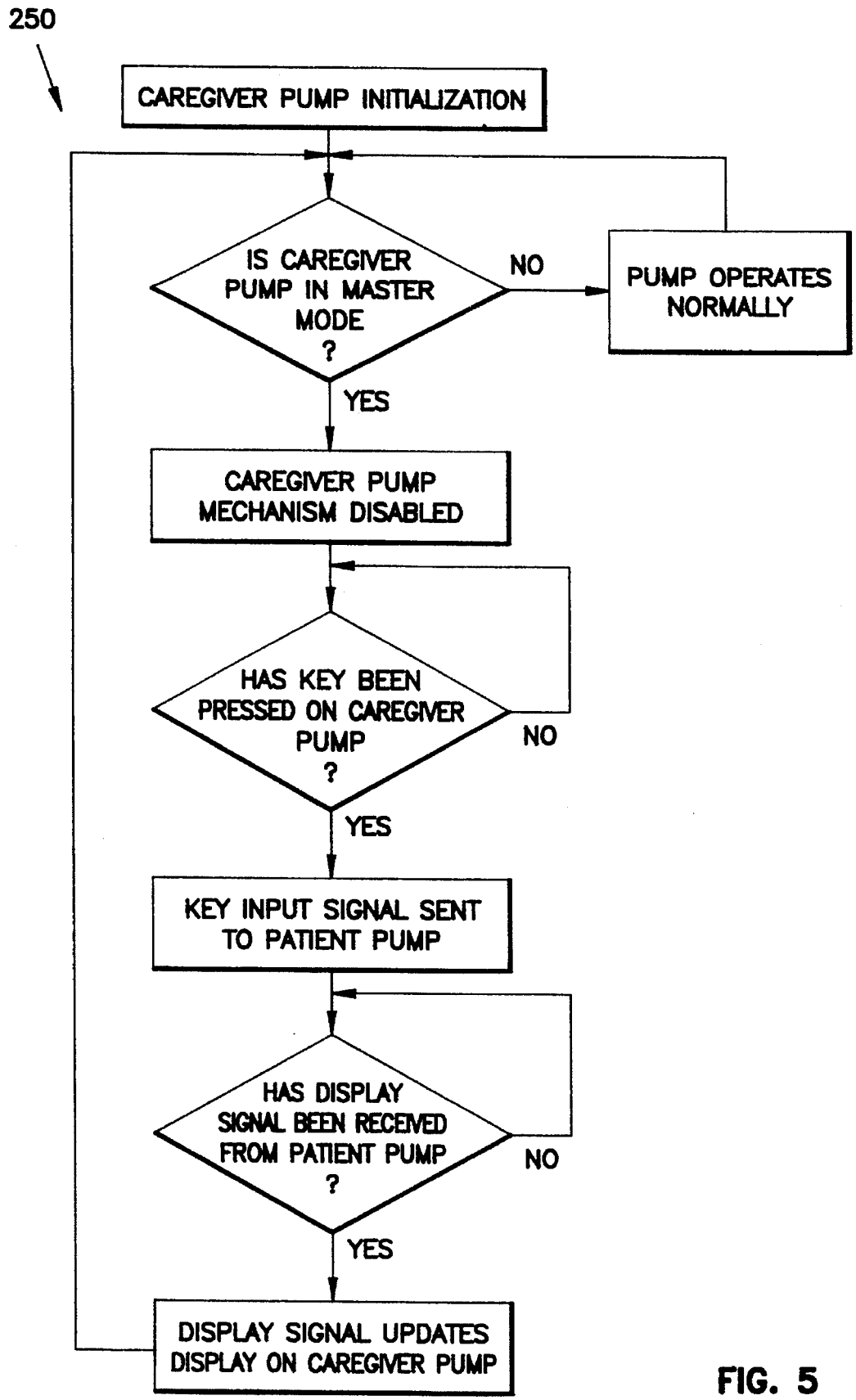
FIG. 5 is a flow chart of an operational sequence of the caregiver pump with respect to the normal pumping mode for pumping fluid and the master mode for pump to pump communication.

Referring now to FIG. 4, a flow chart 200 is shown illustrating one preferred operational sequence of patient pump 40 with respect to the normal pumping mode and the slave mode. FIG. 5 is a flow chart 250 illustrating one preferred operational sequence of caregiver pump 20 with respect to the normal pumping mode and the master mode. FIGS. 4 and 5 illustrate the operational sequences for each pump with respect to normal pumping operations mode, or pump to pump communications operations mode (slave and master modes). FIGS. 4 and 5 specifically show the sequences with respect to communicating the key input signals and the display signals between the pumps.

Referring now to FIGS. 6A and 6B, a flow chart 300 is shown for more specific operational sequences followed during connection and communication between caregiver pump 20 and patient pump 40, respectively. Flow chart 300 of FIGS. 6A and 6B includes a caregiver sequence 302 in the left hand column and a patient sequence 304 in the right hand column. Flow chart 300 also includes actions to be taken by the patient and the caregiver during connection and communication between the two pumps.

The flow chart 300 of FIGS. 6A and 6B shows various steps including the step of hitting the ENTER key. The ENTER key is one key of keys 24 on caregiver pump 20 and keys 44 on patient pump 40.

If a caregiver wanted to monitor or program a patient's pump 40 over the phone line 54, the caregiver and the patient would first contact each other, such as by voice communication over the telephone 29,49, as shown in FIG. 1, to begin initiation of pump to pump communication. Telephones 29,49 may be conventional telephones including means for dialing another phone, and a handpiece or other device for permitting voice communication with the party on the other end. Prior to initiation of pump to pump communication, both pumps 20,40 are in the normal pumping mode. At the top of each column 302,304 of FIG. 6A, pumps 20,40 are in the normal pumping mode. As shown in FIG. 6A, the caregiver would first instruct the patient to connect pump 40 to modem 48, thereby automatically stopping the pump and selecting the appropriate processor program for the slave mode.

Automatic selection of the slave mode and stoppage of the normal pumping mode in patient pump 40 is provided using suitable logic circuitry and sensor structure, such as sensor 49 in FIG. 1A, to sense the presence of cable 50. Automatic selection of the slave mode and stoppage of normal pumping mode by inserting cable 50 into patient pump 40 is useful since it eliminates one or more keyboard entries that might otherwise be necessary by the patient or caregiver to place patient pump 40 in the slave mode from the normal pumping mode. Alternatively, the patient may have to hit a predetermined key 44 or flip a suitable switch to exit the normal pumping mode and enter the slave mode if no automatic selection of the slave mode and automatic stoppage of the normal pumping mode is provided.

In FIG. 1A, sensor 49 is interconnected to communications port 42 through connection structure 49b, and to controller 41 through connection structure 49a. Sensor 49 may include two spaced apart pins which engage the communication cable 50 to close an electrical loop when the cable 50 is operatively positioned in communications port 42. Closure of the loop sends a suitable signal to controller 41 that the cable 50 is present and pump to pump communications is desired, i.e. the slave mode operations program.

The operating system of caregiver pump 20 shall allow the pump to be placed in the caregiver mode of remote programming from the normal pumping mode of operation. Automatic selection of the master mode and automatic stoppage of the normal pumping mode in caregiver pump 20 is provided using suitable logic circuitry and sensor structure to sense the presence of cable 30, such as with a similar sensor to sensor 49 of patient pump 40. Alternatively, the caregiver may have to hit a predetermined key 24 or flip a suitable switch to exit the normal pumping mode and enter the master mode if no automatic selection linked to insertion of cable 30 is provided.

Caregiver pump 20 operating in the master mode includes program means for initiating a modem link to the patient pump 40 operating in the slave mode, as shown in flow chart 300 of FIGS. 6A and 6B. The phone connection to the patient pump 40 shall be assumed to be open. When the modem link between the pumps is established, each time the caregiver presses a key 26 on caregiver pump 20, a key input signal is sent by program means in the controller of caregiver pump 20 to patient pump 40. Program means in patient pump 40 responds to the signal as if it were a key pressed on its own keyboard. Once the processor of patient pump 40 responds to the key input signal, program means in the controller of patient pump 40 sends the updated display signal to caregiver pump 20.

As shown in FIG. 6B, patient pump 40 sends its current display to caregiver pump 20 once the pumps are first linked together. In pump to pump communications, the controllers are preferably menu driven and the current display lets the caregiver see the current status of the patient pump 40 before the caregiver begins to send key input signals to patient pump 40 to obtain the desired information from the patient pump. Following the display on display 26 of the current information on display 46, caregiver pump 20 receives its displays sent to caregiver pump 20 in response to the key inputs to caregiver pump 20 which are sent to patient pump 40.

Instead of an automatic initiation of the modem link to patient pump 40 operating in the slave mode, the caregiver and the patient could both hang up their respective phones after the modem cables were connected. Patient pump 40 is programmed to instruct modem 48 installed at the patient's home to answer the phone the next time it rings. The patient would then wait for the caregiver to call back. Caregiver pump 20 is programmed to instruct modem 28 to call the patient back. Once modem 28 is connected with modem 48, communication between the respective controllers is provided with respect to key input signals and display signals.

In one embodiment, display 46 of patient pump 40 displays everything that is sent to display 26 of caregiver pump 20. In another embodiment, the controller of patient pump 40 is programmed to include a blocking program to block some or all of the information that is sent to the controller of caregiver pump 20 from the controller of patient pump 40 from being displayed on display 46 of patient pump 40 during pump to pump communication. This may be advantageous in keeping some information from the patient, such as controller access codes used to access the processor of patient pump 40 via the keys 44, or keys 24 during pump to pump communications.

If the communication session were interrupted by a bad phone line, patient pump 40 might remain unchanged or partially programmed. During programming of patient pump 40, caregiver pump 20 could get a continuously updated status report from patient pump 40 through appropriate programming in caregiver pump 20 and patient pump 40. The caregiver could review the status report after disconnecting the pump from the modem to verify that patient pump 40 had been programmed as desired by the caregiver.

The controller of each pump 20,40 controls operation of the respective modem 28,48 attached as a peripheral device. The controller of each pump 20,40 instructs its respective modem to go off-hook and disconnect the phone at the initiation of pump to pump communications. The controllers further control operation of a modem speaker associated with each modem so that the patient and caregiver can orally communicate before pump to pump communication begins, and after the voice transmitting and receiving characteristics of one or both of the telephone hand piece have been terminated. The modem speakers are useful if the patient or caregiver is not using the telephone handpiece and such communication is desired. The one party can call to the other through the speaker to pick up the telephone handpiece. Also, the modem speaker lets the caregiver hear predetermined signals from the patient pump 40 during connection to let the caregiver know when the patient pump 40 is ready to begin pump to pump communication, as shown in the flow chart of FIGS. 6A and 6B.

The controller of each pump 20,40 may be provided with masking programs to mask the keys 24,44 which are inactive during pump to pump communication.

Referring now to FIG. 7, a flow chart 400 of a caregiver initiated disconnect operational sequence is shown for disconnecting caregiver pump 20 from patient pump 40. Such disconnect operational sequence is desirable when the caregiver no longer desires communication with patient pump 40. In the flow chart 400 of FIG. 7, a caregiver sequence 402 is shown in the left hand column and a patient sequence 404 is shown in the right hand column. Flow chart 400 describes the various steps during the disconnect sequence initiated by the caregiver. At the top of each column 402,404 of FIG. 7, pumps 20,40 are in the master and the slave modes, respectively.

Attempting to start the caregiver pump 20 is one method of signalling to the controller to terminate the pump to pump communication. The controller of caregiver pump 20 begins the disconnection sequence with respect to modem 28. The controller of caregiver pump 20 further requests that patient pump 40 begin the disconnection sequence with respect to modem 48.

The operating system of each controller allows for automatic disconnection of the respective modems at the conclusion of pump to pump communication, as shown in FIG. 7. The controllers further control operation of the modem speaker so that the patient and the caregiver can orally communicate after pump to pump communication, such that the caregiver can instruct the patient during the disconnect procedures prior to telephone voice communication through the telephone handpiece of the patient.

Program means is provided with patient pump 40 to control operation of a beeper, other sound alarm, or other pump to patient indicator to inform the patient of the upcoming disconnection, as noted in flow chart 400 of FIG. 7. The beeping or other signal may continue until the disconnection is complete. This is useful in informing the patient when the pump to pump communications disconnection procedure begins and when it ends such that the pump is ready to be used in the normal pumping mode.

Referring now to FIG. 8, a flow chart 500 for a patient initiated disconnect operational sequence is shown. The flow chart of FIG. 8 shows a caregiver sequence 502 in the left hand column and a patient sequence 504 in the right hand column. At the top of each column 502,504 of FIG. 8, pumps 20,40 are in the master and slave modes, respectively.

In the flow charts of FIG. 7 and 8, it is noted that the caregiver and the patient press the STOP/START key. The STOP/START key is another one of the keys on keys 24,44 of pumps 20,40. If the pumps are not in the normal pumping mode during pump to pump communication, as is the case in one embodiment, then the STOP/START key is a convenient means for sending a signal to the respective controllers that a discontinuation of the pump to pump communications session is desired by the patient or the caregiver.

As shown in FIG. 8, attempting to start patient pump 40 using the STOP/START key on patient pump 40 is a one method of signalling to the processor to terminate the pump to pump communication. Patient pump 40 requests that caregiver pump 20 begin the disconnection sequences. Patient pump 40 waits for caregiver pump 20 to initiate the disconnect process. The controller of caregiver pump 20 begins disconnection with modem 28, and the controller of caregiver pump 20 further requests that controller of patient pump 40 begin the disconnection sequence with respect to modem 48. It is to be appreciated that when patient pump 40 receives a key input signal from the patient to begin disconnection of the pump to pump communications connection, caregiver pump 40 may continue until caregiver desires to terminate the pump to pump communications connection. The caregiver presses a key, such as the STOP/START key, as noted in FIG. 8 to begin the disconnection sequence at the desired time.

As in the caregiver disconnect sequence of FIG. 7, the disconnect sequence of FIG. 8 includes the controllers controlling operation of the modem speakers so that the patient and the caregiver can orally communicate after pump to pump communication, so that the caregiver can instruct the patient during the disconnect procedures prior to telephone voice communication through the handpieces.

Program means is provided with patient pump 40 to control operation of a beeper or other sound alarm or patient indicator to inform the patient of that the disconnection requested by the patient is upcoming, as noted in flow chart 500 of FIG. 8. The beeping or other signal continues until the disconnection is complete. The audible or other patient signal may be used in combination with or in alternative to the use of the modem speaker at the patient site to indicate to the patient when the cable 50 is to be disconnected from patient pump 40.

Program means is provided with caregiver pump 20 to control operation of a beeper or other sound alarm or caregiver indicator to inform the caregiver that the disconnection has been requested by the patient. This is a page type function where the caregiver can continue with pump to pump communication, or start the disconnect sequence by pressing the STOP/START key.

In some applications, the controller of patient pump 40 is locked, at least partially, via an access code program to prevent the patient from altering the pump operations program or from accessing other information in the memory. In one preferred embodiment, the caregiver can unlock the pump lock of patient pump 40 from a remote location via the pump to pump communication system. Preferably, the caregiver can then relock the pump lock of patient pump 40 after the caregiver has adjusted or changed the pump operations program. Automatic relock program means may be provided to automatically relock the controller at the conclusion of the caregiver's access of the controller to change the operating programs.

Figure 2:
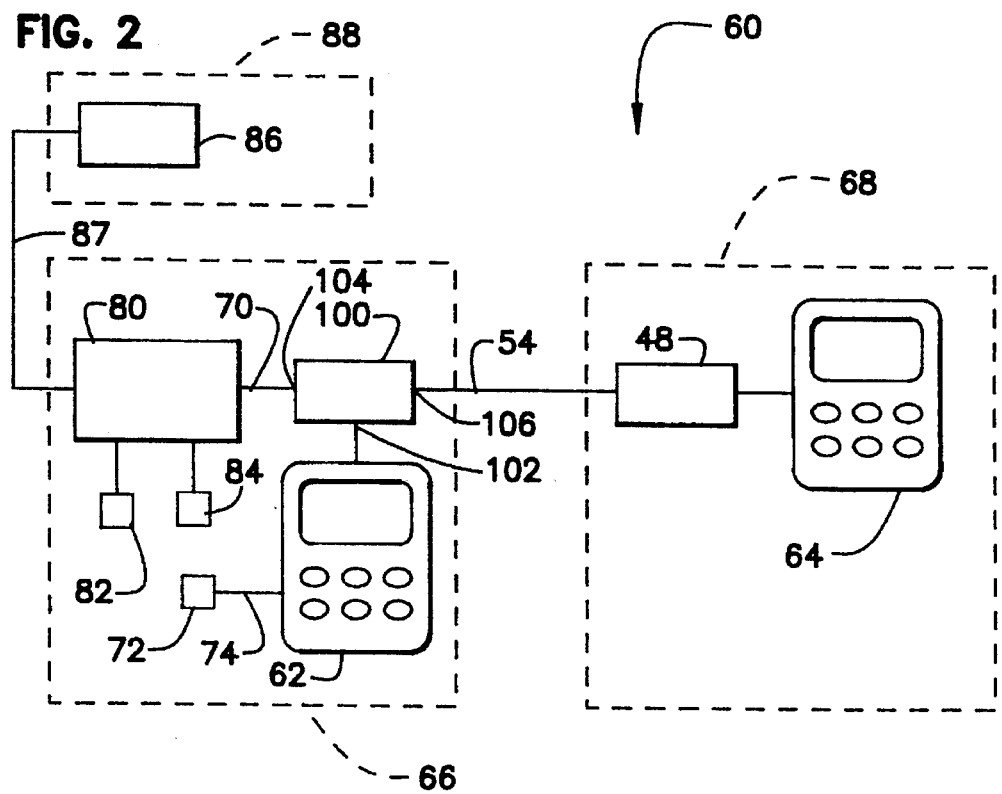
FIG. 2 is a schematic diagram illustrating a second system using a personal computer to communicate with a local pump and/or a remote pump. Local pump and remote pump communications capability is also shown.

Referring now to FIG. 2 where an alternative embodiment is shown, the schematic diagram illustrates a communication system 60 for communication between pump 62 and a computer 80, both located at caregiver's office 66. Pump 62 may be a caregiver pump, like caregiver pump 20, or a patient pump, like patient pump 40.

FIG. 2 also illustrates communication between a patient pump 64, located at the patient's home 68, and both computer 80 and pump 62. It is to be appreciated that in some applications, pump 62 may not be present. Also, it is to be appreciated that in some applications pump 64 may not be present. In either of those applications, computer 80 would be communicating only with the remaining pump.

An example of computer 80 includes an 80386 INTEL microprocessor, with 2 megabytes of RAM and operated by commercially available operations software such as DOS, UNIX, and others and further programmed with application specific program functions to communicate with pumps 62,64 and carry out the specified tasks desired by the caregiver. A suitable keyboard may be provided with computer 80 to make operator inputs to the microprocessor.

As shown in FIG. 2, computer 80 may further communicate with a second computer 86 to transfer data and or programs to and from computer 80 over communications medium 87, such as conventional telephone lines. For example, computer 80 may be located at the caregiver's office 66, such as a hospital. The second computer 86 may be located at the pump manufacturer's/servicer's facilities 88. The second computer may receive and transmit information to a plurality of computers 80. This arrangement may be useful for maintaining a plurality of patient pumps 64, through a plurality of caregiver's offices 66. Also, improved drug therapies may result if the pump manufacturer/servicer has ready access to patient pump usage data.

Pumps 62,64 are preferably identical mechanically and electrically to pumps 20,40 described previously. In some situations, the controllers of pumps 62,64 may be programmed differently, depending on how the pumps are to be used. Pump 64 is typically used as a patient pump. As a patient pump, pump 64 requires the normal pumping mode operating program and the slave mode operating program at minimum.

In system 60, pump 62 may be a patient pump or a caregiver pump. As a patient pump, pump 62 requires the normal pumping mode operating program and the slave mode operating program at a minimum. Pump 62 as a patient pump is present at the same site as computer 80 such as when pump 62 is brought in by the patient. In some situations, pump 62 may be a patient pump that is in the caregiver's office 66 for data gathering, trouble shooting, and/or program changes or modifications. Also, before the patient leaves the caregiver's office 66, pump 62 is present in caregiver's office 66 for use as a patient pump in the caregiver's office. As a caregiver pump, pump 62 requires the master mode operating program at a minimum. Pump 62 operating as a caregiver pump may also include the normal pumping mode operating program and the slave mode operating program.

Figure 3:
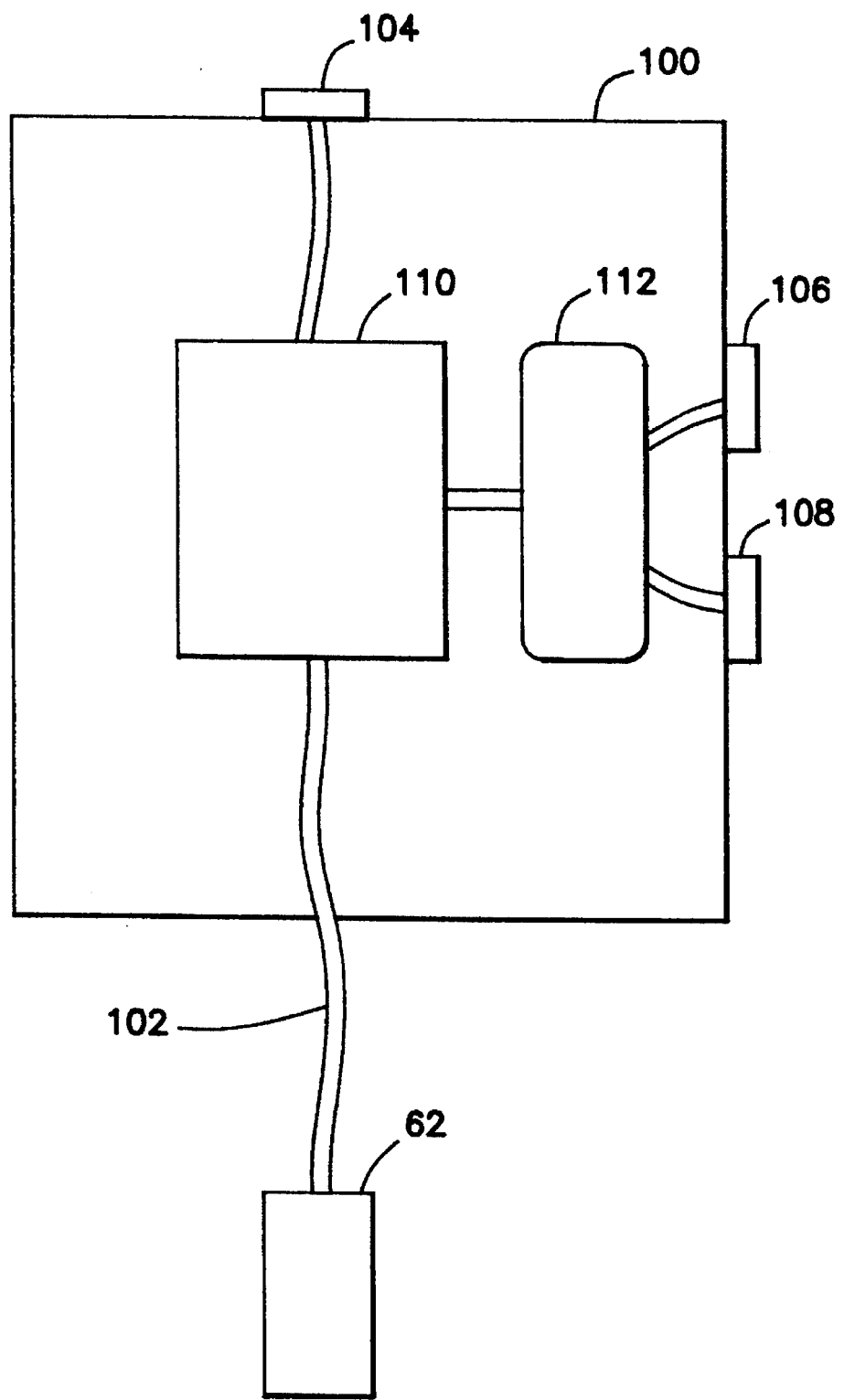
FIG. 3 is a schematic diagram of a modem useful in the communication system shown in FIG. 2 to interconnect a personal computer, a local pump, and a remote pump.

To permit communication between pump 62, computer 80, and pump 64, a modem 100 is provided. Referring now to FIG. 3, modem 100 is shown in additional detail. Modem 100 includes a local pump communications cable 102 for electrical connection of modem 100 to a local pump such as pump 62 shown in FIG. 2. Cable 102 is like cables 30,50 of FIG. 1. Cable 102 extends from modem controller 110 for selective connection to pump 62.

Modem 100 further includes a computer communications port 104 for electrically linking modem 100 with computer 80 as shown in FIG. 2.

Modem 100 further includes a phone system communications port 106 for electrically linking modem 100 to remote sites over communications medium 54. In the embodiment shown, communications port 106 permits interconnection of modem 100 with modem 48 over the telephone lines 54, as shown in FIG. 2. Such interconnection permits communication between modem 100 and patient pump 64, located at a remote site from modem 100.

Modem 100 further includes a local phone communications port 108 to permit interconnection of a local phone (not shown) with modem 100. Local phone port 108 permits use of a local phone such that the caregiver can communicate by conventional telephone voice communication with the patient, before a modem link is established and after the modem link is terminated.

Modem 100 permits information to be transmitted from computer 80 to a remote site over the phone lines 54. Modem 100 further permits pump 62 to communicate with the remote site over phone lines 54. Remote communication with pump 64 over the phone lines through modem controller 110 and modem module 112 is preferably at 9600 bps (bits per second). Modem 100 preferably includes error correction and data compression capabilities.

Modem 100 further permits communication between pump 62 and computer 80. Preferably, such communication is at 19,200 bps through the modem controller 110 in a pass through configuration. Pump 62 is preferably not linked directly to computer 80, since pump 62 may be provided with different power supplies other than conventional 110 volt power supplies used to power computer 80. Also, it is desireable to electrically isolate pump 62 from computer 80 to protect pump 62 and the patient from hazards of the electrical source powering computer 80, such as electrical shock. Preferably, modem 100 communicates with computer 80 through appropriate connection structure, such as an RS232 serial cable.

FIG. 2 also shows pump 62 interconnected to its own stand alone printer 72 interconnected with connection structure 74, such as an RS232 serial cable. Parallel communication may be used, instead of serial communication. Printer 72 produces a hard copy of information stored in the controller of pump 62. In some cases, printer 72 would be useable only through the communications port which connects pump 62 to modem 100, as shown in FIG. 2. In other words, pump 62 may not be useable simultaneously with printer 74 and modem 100. An appropriately sized controller and two communications ports would permit such usage.

Communication between computer 80 and a pump, whether remotely (with pump 64) or locally (with pump 62) is useful for several reasons. First, computer 80 may be provided with greater memory and data processing capabilities than exist with the individual pumps 62,64. Printing capabilities may be greater with a printer 82 electrically interconnected to computer 80. Display capabilities may be greater with a monitor 84 electrically interconnected to computer 80. Also, computer 80 may be useful in the recertifying operations of the pumps periodically, as required to verify operability and accuracy of the pumps.

Computer 80 also may be useful for making program adjustments or application changes in the pumps 62,64. For example, drug delivery devices may be used in a variety of normal pumping modes, or applications, such as 1) pain control; 2) nutrition; 3) chemotherapy; and 4) antibiotic therapy. Other applications are possible.

Each of the applications may involve different operations of the pumping mechanism. Each application may have one or more patient specific variations on operation of the pumping mechanism and other pump control functions. Also, some of the applications may involve some patient input, such as is sometimes the case in pain control applications. For example, if the patient is experiencing pain at a particular time, the caregiver may provide for increased dosages as needed by the patient, within specified parameters such as time and amount. In this application, the pumping mechanism needs to be operable automatically, and at the discretion of the patient, within the specified parameters. The operating program contains the appropriate pump control commands for controlling the pumping mechanism and the functions of the keys which permit patient control of the pumping mechanism. The other applications may include different pump control commands and different functions of the keys. Within each of the four applications listed above, various different pump operations programs may exist. The controller of the patient pump 40 may be appropriately programmed by the caregiver for the specific patient usage.

It is to be appreciated that the caregiver pump 20 and the patient pump 40 do not need to include the same application program for operating the pumping mechanism. A significant advantage of the present invention is that the caregiver can communicate successively with different patients, with each patient involving a different pump application, or each patient involving the same pump application with different patient specific functions. At a minimum, it is preferred that caregiver pump 20 includes the master mode operations program, and that patient pump 40 includes the slave mode operations program and one application or normal pumping mode operations program for operating the pumping mechanism to pump fluid to the patient. Preferably, it is more convenient for the caregiver if caregiver pump 20 and patient pump 40 include both the slave mode operations program and the master mode operations program, and also at least one normal pumping mode operations program.

It is anticipated that the caregiver can locally or remotely program the controllers of pumps 20,40,62,64 such that the pump operates either in 1) the normal pumping mode or slave mode, or 2) the normal pumping mode or the master mode at the initiation of the pump to pump communications sequences.

Various pump related data may be stored in the controllers of pumps 20,40. Information which may be gathered during use of patient pump 40 includes date and time of:

1) Pump Error Conditions, for example, where the pumping mechanism has stopped and a suitable sensor sends a pump stoppage signal to the processor.

2) High Pressure Alarm for Downstream Blockages, where a suitable pressure sensor sends a high pressure signal to the processor.

3) Upstream Occlusion Alarm, where a suitable pressure sensor sends an occlusion signal to the processor.

4) Any Fluid Reservoir Removal Event, where a suitable sensor sends a reservoir removed signal to the processor.

5) Any Fluid Reservoir Attached Event, where a suitable signal is sent to the processor by a suitable sensor, possibly the same sensor as the sensor for sensing a reservoir removed event.

6) Any Internal Battery Event, where a suitable sensor senses whether the battery has been changed, is low, or is depleted.

7) Any AC Adaptor Event, where a suitable sensor senses whether the adapter is connected, disconnected, or unplugged from the wall outlet.

8) Any portable Power Pack Event, where a suitable sensor senses whether the power pack is connected, disconnected, or depleted.

9) Any Remote Dose Cord Event (which permits patient to remotely press a key, such as the DOSE key on the keypad), where a suitable sensor senses whether the dose cord is connected or disconnected.

10) Any Communications Cable Event (to permit the pump to communicate with a printer, another pump or a computer), where a suitable sensor senses whether the cable is connected or disconnected.

11) Anytime the Device is Successfully Stopped or Started with START/STOP key, where a suitable sensor senses whether the pump is successfully stopped or started after the key is pressed.

12) Any Lock Level Change and the New Lock Level, in situations where the amount of access to the processor by the patient is changed, i.e. full access, some access, no access.

13) Any Patient Pump Operational Program Change or Status Reset/Clear in the New Program.

14) Anytime the PRIME key is used and how much fluid is primed to get air out of the pump, such as during pump start up.

15) Any Patient Dose Delivered and the Amount Delivered by the patient hitting the DOSE key to manually give the patient an additional amount of fluid.

16) Any Change in Other Features (units, time or date set, auto lock change, application change) and the New Data or State.

17) Anytime the Pump is Successfully Recertified.

18) Number of Activations of Pumping Mechanism and Duration of Use.

Various functions are anticipated for each of the keys on each pump 20,40. Each key has at least one function. Examples of potential functions of the different keys include:

1) A NEXT SCREEN key to move through the various screens by running a next screen program;

2) An ENTER/CLEAR key;

3) AN UP ARROW key and a DOWN ARROW key for paging through what is displayed on the screen with a highlight bar, or to page through numeric values to highlight and/or display the desired value;

4) A PRIME key to run a pump prime program to prime the pump;

5) A START/STOP key for operating a pump start program and a pump stop program;

6) A LOCK key for providing access control to the processor through an access program;

7) A DOSE key to run a patient pump control program for permitting patient control of the pumping mechanism;

8) A HELP key for providing help information on the display.

Figure 9:
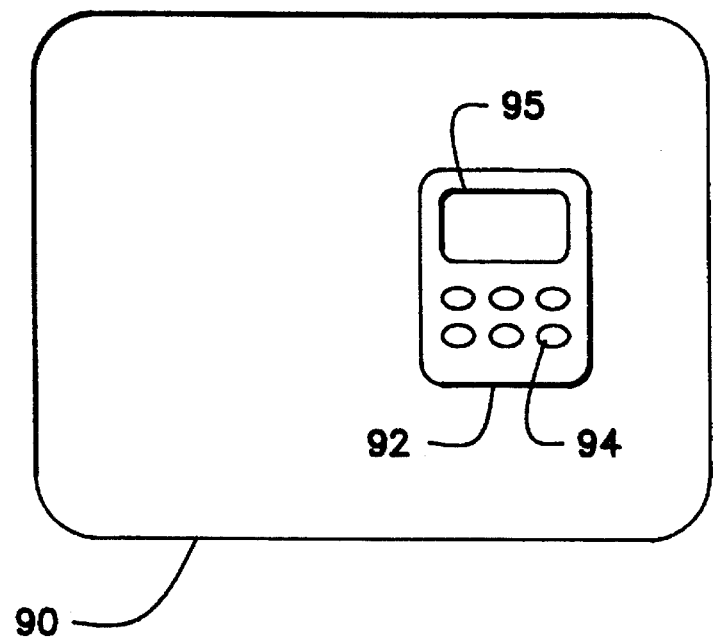
FIG. 9 is a schematic diagram showing a computer screen displaying an image of a pump, as part of a computer system used for communicating with a pump.

Referring now to FIG. 9, a monitor or computer screen 90 is shown, as another embodiment of the invention. An image of a pump 92 (front view) is displayed on screen through suitable graphics capability. Screen 90 is operatively interconnected with a processor of computer system, such as the processor of computer 80. The image 92 on screen 90 is able to be manipulated as if it were a pump through the use of a screen interactive program utilizing a mouse or a touch screen. Computer 80 is programmed to run various programs depending on how the various keys 94 of pump image 92 are pressed through the use of the mouse or the touch screen. This permits simulation of the pump 20 with the use of a computer 80. Display area 95 may then display information like display 26 of pump 20.

Computer screen 90 and computer 80 are utilized to communicate with a pump located at a remote site, like pump of FIG. 2. If the pump is located locally, like pump 62 of FIG. 2, then communication is direct with a straight through pass as shown in FIGS. 2 and 3.

The arrangement involving the computer screen of FIG. 9 is useful when the caregiver is communicating with a patient pump at a remote location or at a local location. The caregiver can more easily use the computer system since the caregiver is already familiar with the operation of a pump through the use of the keys and the display. Activating the keys 94 of the image 92 and using the display 95 of the pump image simulates for the caregiver the presence of an actual pump. This facilitates reductions in training time for training the caregiver to communicate with the patient's pump, since the caregiver is most likely already familiar with operation of the patient's pump.

The computer system with the pump image program may also be used as a simulator for training the caregiver and/or the patient how to use the pump. The simulator includes various programs for simulating operation of a patient's pump to pump fluid. The simulator also includes various programs for simulating various communication situations with a patient's pump.

Figure 10:
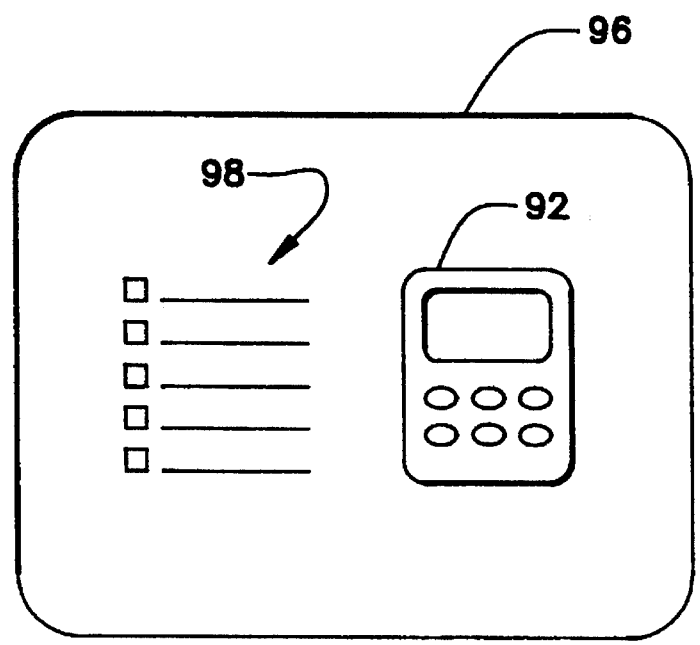
FIG. 10 is a schematic diagram showing a second computer screen displaying an image of a pump, as part of a computer system, and including information displayed on the screen relating to simulation sequences for use in training.

As shown in FIG. 10, a computer screen 96 of a training simulator system is shown. On computer screen 100, pump image 92 and simulator information 98 are displayed. Simulator information is used to select various conditions through simulator programs for simulating a operation of a patient pump. Pump 92 could function as a caregiver pump to permit training of a caregiver on how to use the caregiver pump to communicate with a patient pump. For example, if the caregiver trainee wanted to simulate a communications session with a remote patient pump that had a low battery, for example, the caregiver trainee would select the program in listing 98 that would simulate a pump to pump communications situation where the caregiver would trouble shoot the patient pump to determine that a low battery situation existed. The simulator also has a simulator program for simulating at least some of the sequences to connect and disconnect the pumps according to the flow charts of FIGS. 6A, 6B, 7, and 8.

The simulator system also includes simulation programs in information 98 for simulating operation of the pump on the screen 96 as a patient pump to pump fluid to a patient. This would be useful for training a patient and a caregiver how to operate the pump in the normal pumping mode.

The present invention relates specifically to a pump communication simulator for training a pump operator comprising: a computer system including processor means, and display means electrically interconnected to the processor means of the computer system; first program means for displaying an image of the pump on the display means, the image having an input region and a display region; second program means for permitting manipulation of the input region of the image of the pump on the display means by the pump operator such that access to the processor means of the computer system is achieved; and third program means for sending a predetermined message to the display region of the image of the pump in response to manipulations of the input region of the image by the pump operator.

The invention is not to be construed as to be limited by the specific embodiments described above or shown in the drawings, but is to be limited only by the broad general meaning of the following claims.

What is claimed is:

1. A pump simulation system for simulating a medical pump for intravenous delivery of a fluid, the pump simulation system comprising:

a computer system including processor means, and display means electrically interconnected to the processor means of the computer system;

first circuitry configured to generate a graphical user interface having an image of the medical pump, the graphical user interface being generated on the display means and having an input region and a display region;

second circuitry configured to permit manipulation of the input region of the graphical user interface by an operator such that access to the processor means of the computer system is achieved; and third circuitry configured to generate and send a predetermined message to the display region of the image of the pump in response to manipulations of the input region of the image, thereby simulating operation of the pump.

2. An apparatus for simulating a medical pump, wherein the medical pump has keys and a visual display, further wherein the medical pump is responsive to activation of a predetermined sequence of keys, the apparatus comprising:

a display screen;

an input device; and a processor having:

a pump-image file configured to generate a graphical user interface on the display screen, the graphical user interface including an image of the medical pump, the graphical user interface having an input region and a display region, the input region having a plurality of input portions, wherein each input portion corresponds to one of the keys on the medical pump, further wherein each input portion is configured to be activated by the input device thereby simulating activation of the keys; and a pump-simulation file, wherein activation of the predetermined sequence of keys, as simulated by activation of the input portions, will cause the pump-simulation file to generate information in the display region, thereby simulating operation of the medical pump.

3. The apparatus of claim 2 wherein the pump-simulation file is configured to simulate operation the medical pump as it is pumping fluid.

4. The apparatus of claim 3 wherein the pump-simulation file is configured to simulate an error condition, further wherein activation of the predetermined sequence of keys, as simulated by activation of the input portions, will correct the simulated error condition.

5. The apparatus of claim 2 wherein the medical pump can be controlled by a remote unit, the processor further having a communication-simulation file configured to simulate communication between the remote unit and the medical pump.

6. The apparatus of claim 5 wherein the communication-simulation file is configured to simulate establishing and disconnecting a communication link between the remote unit and the medical pump.

7. The apparatus of claim 5 wherein the pump-simulation file is configured to simulate the remote unit, the remote unit being a second medical pump.

8. The apparatus of claim 5 wherein the pump-simulation file is configured to simulate the remote unit, the remote unit being a computer that simulates the medical pump.

9. The apparatus of claim 2 wherein the input device includes a touch-sensitive transducer cooperatively connected to the display screen.

10. The apparatus of claim 2 wherein the input device is a mouse.

* * * * *